United States Patent [19]

Wuhr

[11] Patent Number: 5,660,947
[45] Date of Patent: Aug. 26, 1997

[54] ELECTROLYTE FOR USE IN A GALVANIC CELL

[76] Inventor: Manfred Wuhr, Erikaweg 53b, D-93053, Regensburg, Germany

[21] Appl. No.: 545,592

[22] PCT Filed: Apr. 29, 1994

[86] PCT No.: PCT/EP94/01366

§ 371 Date: Feb. 20, 1996

§ 102(e) Date: Feb. 20, 1996

[87] PCT Pub. No.: WO94/27335

PCT Pub. Date: Nov. 24, 1994

[30] Foreign Application Priority Data

May 13, 1993 [DE] Germany ............... 43 16 104.9

[51] Int. Cl.$^6$ ............... H01M 6/16; H01M 6/14; H01M 6/04

[52] U.S. Cl. ............... 429/192; 429/194; 429/197; 429/198; 429/201; 429/199

[58] Field of Search ............... 429/197, 194, 429/199, 201, 190, 191, 192, 198

[56] References Cited

U.S. PATENT DOCUMENTS 4,808,282  2/1989  Gregory ............... 204/58.5

FOREIGN PATENT DOCUMENTS

| | | |
|---|---|---|
| 0122381 | 10/1983 | European Pat. Off. |
| 0538615 | 4/1985 | European Pat. Off. |
| 55-165580 | 3/1981 | Japan |
| 58-068878 | 7/1983 | Japan |
| 1157514 | 9/1989 | Japan |
| 4-48709 | 5/1992 | Japan |
| 2143228 | 2/1985 | United Kingdom |

OTHER PUBLICATIONS

B. Scrosati, J. Electrochem. Soc. vol. 139, 2776 (1992), Lithium Rocking Chair Batteries: An Old Concept?.

Barthel, J. et al., J. Electrochem. Soc. vol. 140,6 (1993), The Influence of Water on the Cycleability of Lithium in 2-Methyltetrahydrofuran-Based Electrolytes.

Yilmaz, H. et al., J. Electroanal. Chem. vol. 261,105-112 (1989), Correlation of Anodic Peak Potentials with the Semi-Empirical orbital and HOMO Energies of Various Vinyl Compounds.

*Primary Examiner*—Kathryn L. Gorgos
*Assistant Examiner*—Edna Wong
*Attorney, Agent, or Firm*—Handal & Morofsky

[57] ABSTRACT

Disclosed is a stable and environmentally compatible explosion-safe electrolyte for use in a galvanic cell. The electrolyte comprises salts of the composition $ABL_2$, wherein A is lithium or a quarternary ammonium ion, B is boron, and L is a bidentate ligand which is bound to the central boron atom by two oxygen atoms. Described are the production and the electrochemical properties of several compositions.

20 Claims, 9 Drawing Sheets

1.231 molal $LiB(C_6H_4O_2)_2$ in PC

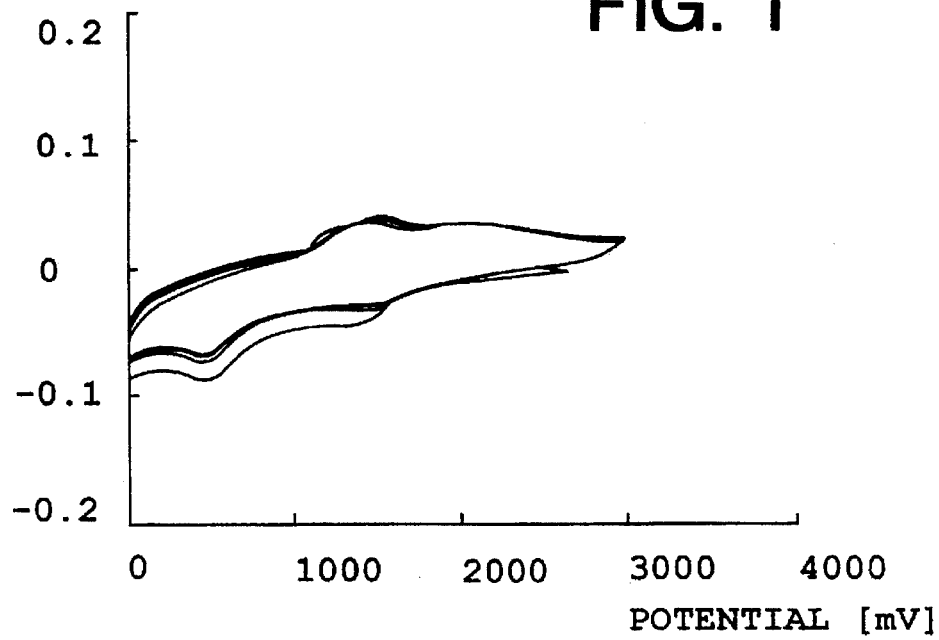
1.231 molal $LiB(C_6H_4O_2)_2$ in PC
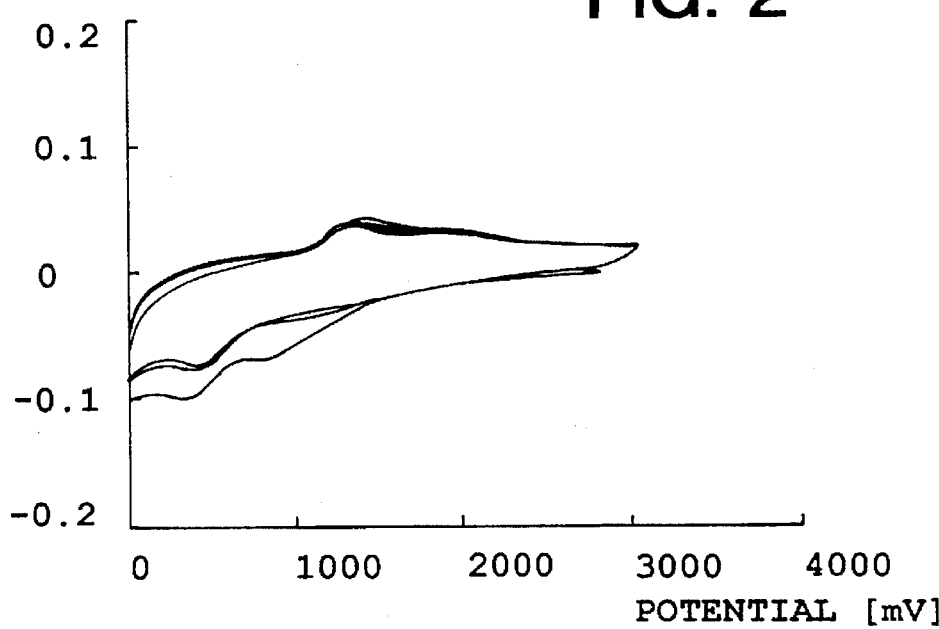
0.293 molal $LiB(C_6H_4O_2)_2$, 0.519 molal $N(CH_3)_4B(C_6H_4O_2)_2$ in PC 0.595 molal LiB(C$_6$H$_4$O$_2$)$_2$ in 2-Me-THF 0.473 molal LiB(C$_6$H$_4$O$_2$)$_2$, 0.896 molal N(CH$_3$)$_4$B(C$_6$H$_4$O$_2$)$_2$
in a mixture of 56,9 weight% PC and 43,1 weight% DME

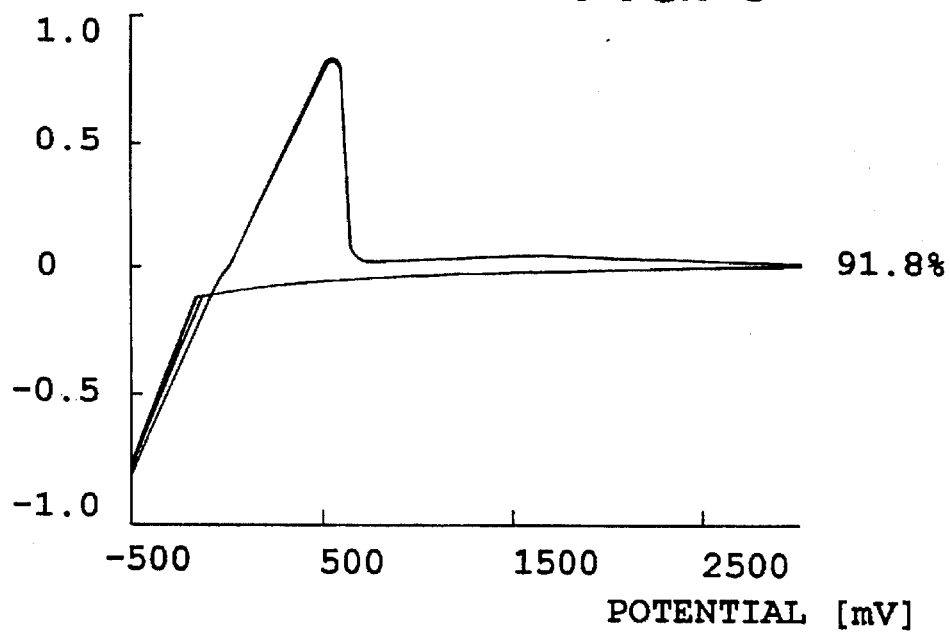
1.231 molal LiB(C$_6$H$_4$O$_2$)$_2$ in PC
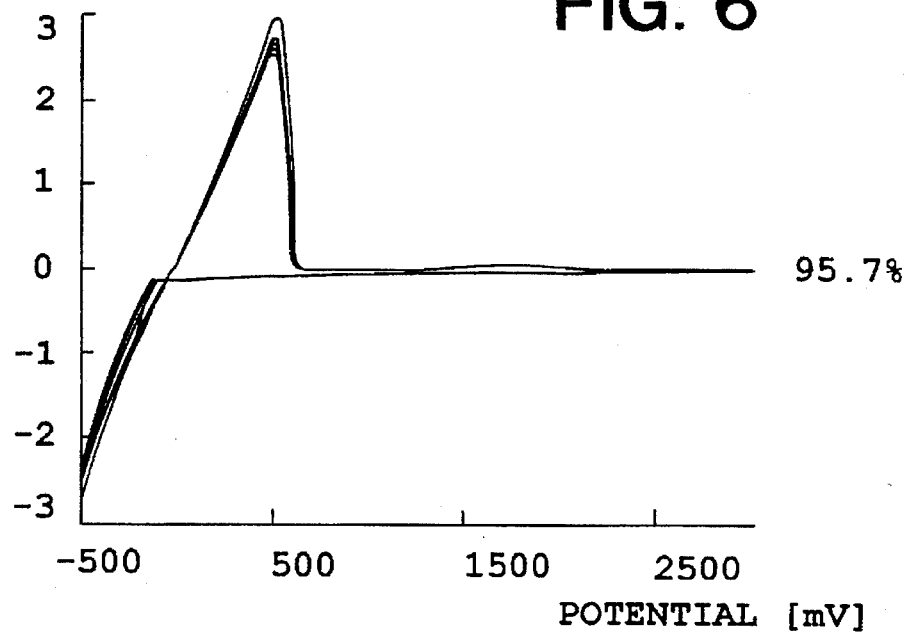
0.293 molal LiB(C$_6$H$_4$O$_2$)$_2$, 0.519 molal N(CH$_3$)$_4$B(C$_6$H$_4$O$_2$)$_2$ in PC

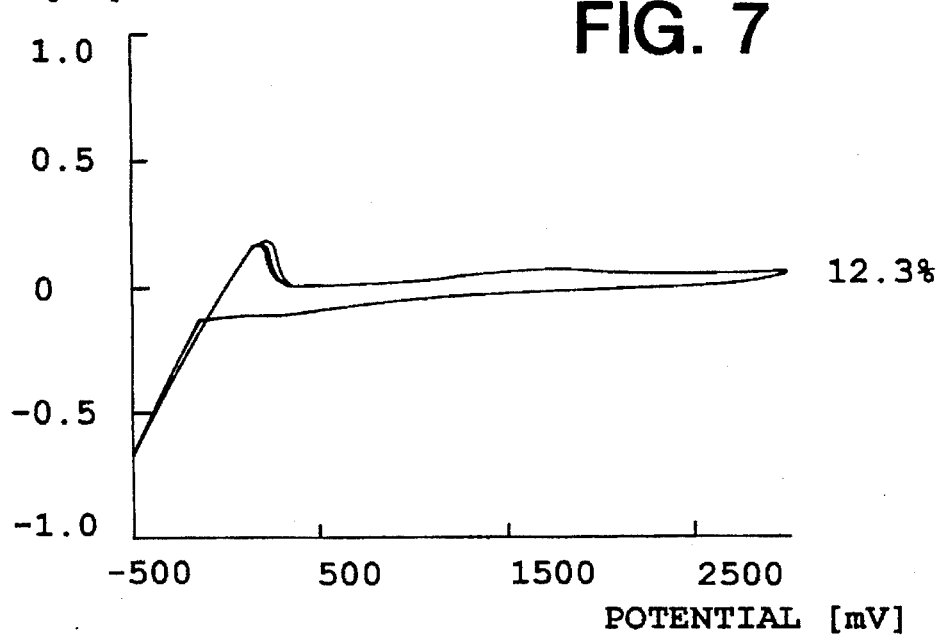
0.595 molal LiB(C_6H_4O_2)_2 in 2-Me-THF
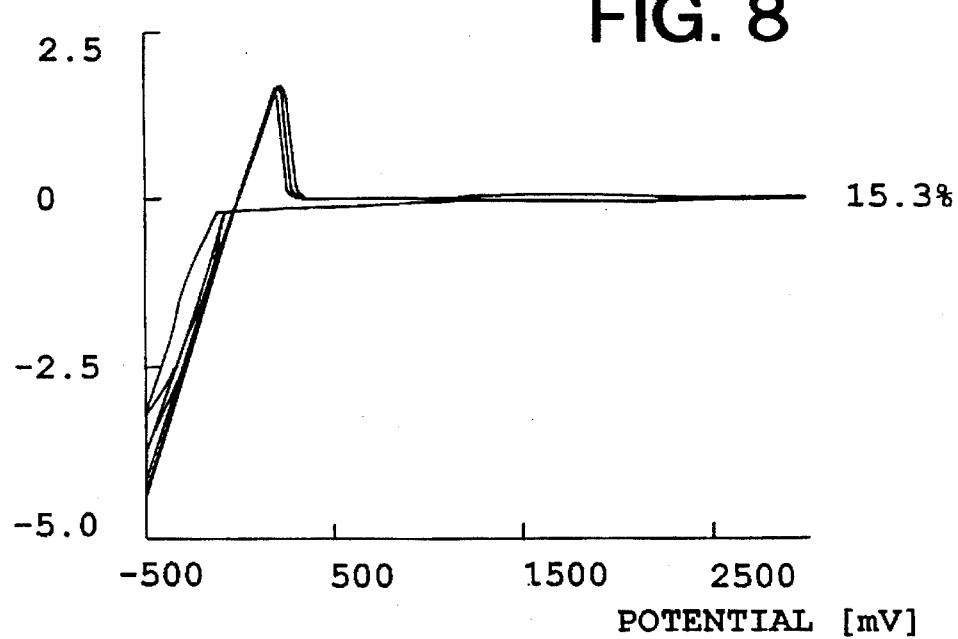
0.899 molal LiB(C_6H_4O_2)_2 in DME 0.473 molal LiB(C$_6$H$_4$O$_2$)$_2$, 0.896 molal N(CH$_3$)$_4$B(C$_6$H$_4$O$_2$)$_2$
in a mixture of 56.9 weight% PC and 43.1 weight% DME 0.473 molal LiB(C$_6$H$_4$O$_2$)$_2$, 0.896 molal N(CH$_3$)$_4$B(C$_6$H$_4$O$_2$)$_2$
in a mixture of 56.9 weight% PC and 43.1 weight% DME 0.473 molal $LiB(C_6H_4O_2)_2$, 0.896 molal $N(CH_3)_4B(C_6H_4O_2)_2$
in a mixture of 56,9 weight% PC and 43,1 weight% DME 1.231 molal $LiB(C_6H_4O_2)_2$ in PC 1.231 molal LiB($C_6H_4O_2$)$_2$ in PC 0.899 molal LiB($C_6H_4O_2$)$_2$ in DME 0.473 molal LiB(C$_6$H$_4$O$_2$)$_2$, 0.896 molal N(CH$_3$)$_4$B(C$_6$H$_4$O$_2$)$_2$ in a mixture of 56.9 weight% PC and 43.1 weight% DME Cycling on carbon Cycling on carbon

1

ELECTROLYTE FOR USE IN A GALVANIC CELL

This is a national stage application of PCT/EP94/01366 filed Apr. 29, 1994.

BACKGROUND OF THE INVENTION AND FIELD OF THE INVENTION

The present invention concerns new electrolytes for use in galvanic cells, in particular lithium cells. In this paper a lithium cell is defined as follows: Essentially a lithium cell consists of an anode, a cathode, and an electrolyte. The anode consists of lithium, a lithium alloy, or a compound which is able to intercalate lithium ions, for example carbon. In general the cathode consists of a substance which is able to intercalate lithium ions or reacts electrochemically with lithium ions, where the potential of the cathode is markedly higher than the potential of the anode. The electrolyte consists of one or more salts which are dissolved in a suitable solvent, a mixture of solvents, a polymer, or a mixture of a polymer with one or more solvents. A distinction is made between primary and secondary lithium cells.

This definition includes the so-called 'rocking chair batteries'. Recent investigations in this field are described in a review of B. Scrosati (J. Electrochem. Soc. Vol. 139, 2776, (1992)).

Typical solvents currently in use include:

Organic carbonates such as propylene carbonate (PC) or ethylene carbonate (EC). Linear and cyclic ethers and polyethers such as dimethoxyethane (DME), diethoxyethane (DEE), tetrahydrofurane (THF), 2-methyltetrahydrofurane (2-Me-THF), dioxolane, and the polymer polyethylene oxide as well.

Typical salts currently in use include:

Lithium perchlorate ($LiClO_4$), lithium tetrafluoroborate ($LiBF_4$), lithium hexafluorophosphate ($LiPF_6$) lithium hexafluoroarsenate ($LiAsF_6$), lithium trifluoromethylsulfonate ($LiCF_3SO_3$), and lithium bis(trifluoromethylsulfonyl) imid ($Li(CF_3SO_2)_2N$).

The above-mentioned salts show some serious drawbacks. Lithium perchlorate has a tendency to explode in combination with some solvents such as dioxolane. Compounds with fluorinated inorganic anions, such as lithium hexafluorophosphate, are of low thermal stability, and generate Lewis acids by dissociation which are able to polymerized the solvent. Because of its arson content lithium hexafluoroarsenate is environmentally damaging, and generates carcinogenic by-products by reaction with lithium. Lithium bis(trifluoromethylsulfonyl)imide is comparatively expensive.

SUMMARY OF THE INVENTION

The object of the present invention is to provide an electrolyte for use in a galvanic cell which is non-explosive, stable, and ecologically harmless and a galvanic cell using the electrolyte.

This is achieved by an electrolyte comprising borates of the formula $ABL_2$, wherein A is lithium or a quarternary ammonium ion. The bidentate chelate ligand L is bonded to the central boron atom via two oxygen atom. In general chelate complexes of this type are of high thermal stability. There is little risk of an exothermic reaction with the solvent or with lithium, because borates are no highly oxidizing agents. Therefore, the electrolytes in accordance with the invention are non-explosive. Furthermore, the salts in accordance with the invention are not able to form Lewis acids, which would polymerized the solvent. Therefore, the electrolytes are stable for a long time and can be used over a wide temperature range. The salts in accordance with the invention comprise no elements which are able to form toxic compounds during combustion. In general hydrolytic products of the salts are harmless and of low toxicity. Therefore, the electrolytes in accordance with the invention are environmentally harmless.

BRIEF DESCRIPTION OF THE DRAWINGS

FIGS. 1 to 9 show cyclic voltammograms of the residual current of some systems of the electrolyte of the disclosed invention:

DESCRIPTION OF THE PREFERRED EMBODIMENTS

Figure 3:
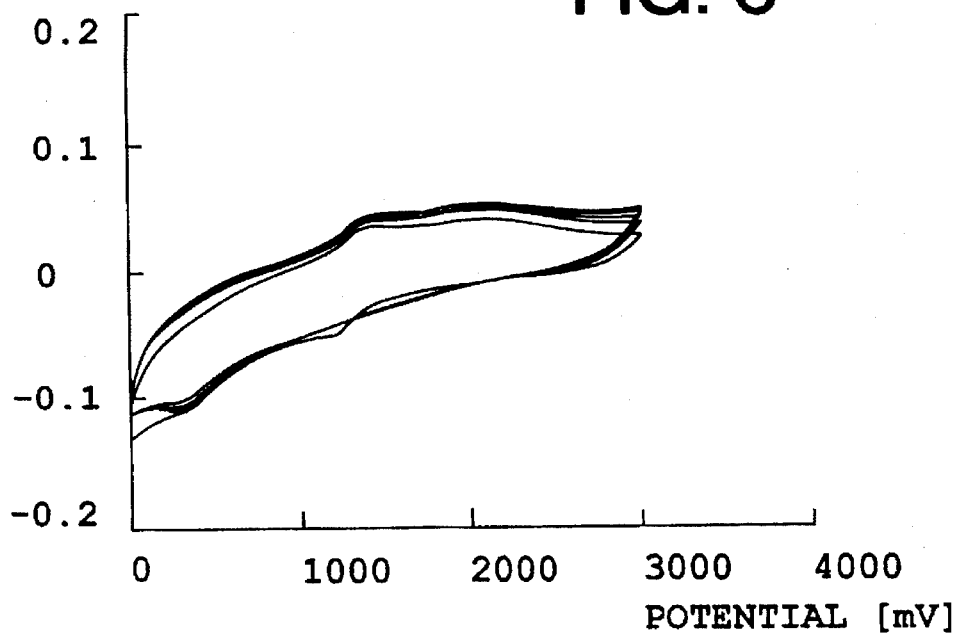
Figure 4:
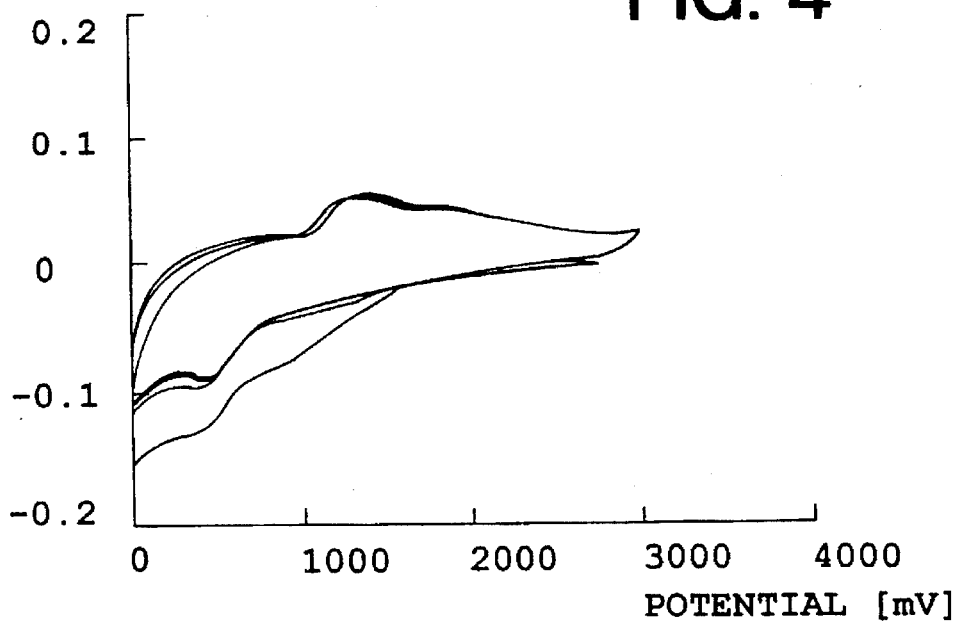
Figure 9:
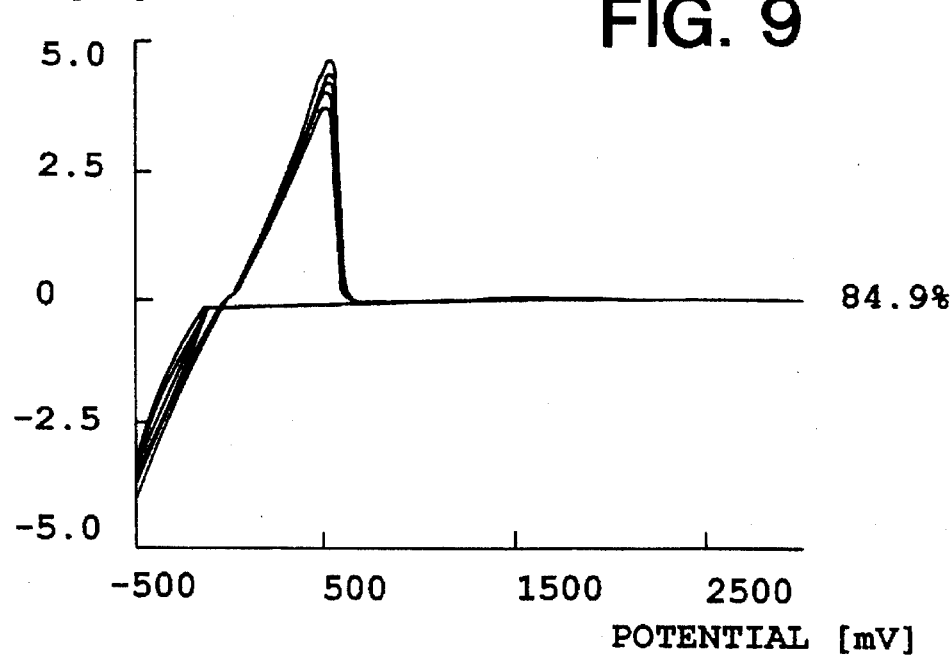

The conductivity of the electrolytes is increased by making electrolytes of the type according to the invention which contain a quarternary ammonium salt in addition to the lithium salt. For example, tetraalkylammonium salts with four alkyl groups (cf. example 2, and 3) or quarternary ammonium salts with spirane structure such as bispiperidenium salts can be used. Furthermore, the residues bounded to the nitrogen atom may contain hereto atoms, as for example in the case of the (2-ethoxyethyl) trimethylammonium ion. Furthermore, the conductivity of the electrolytes is increased by using mixtures of a solvent with high permittivity and a solvent with low viscosity. Data of this type of systems are shown in example 5.

The electrochemical properties of several salts in accordance with the invention were investigated by the methods shown in a paper of Barthel et at. (J. Electrochem. Soc., Vol. 140, 6, (1993)). The examples 6, 7, 9, 10, and 11 demonstrate electrolytes showing excellent cycling behaviour, if they comprise an organic carbonate as a solvent, for example PC.

Two bidentate chelate ligands are linked to the central boron atom by oxygen atoms in the salts according to the invention. There is always a negative partial charge at the oxygen atoms, because oxygen is a highly electronegative element. It is advantageous, if the ligand comprises an aromatic system reducing the electron density respectivty the partial charge, because in this way the negative charge is equal spread over the anion. The interaction between cation and anion is reduced both in solid and in solution. This results in a relative high conductivity and solubility of the compounds in aprotic organic solvents.

The ligand should not be too large, because in this case anion mobility is low resulting in a poor conductivity. Therefore, ligands are advantageous, if they comprise an aromatic six-membered ring.

The delocalisation of the negative charge of the anion is increased, if the ligand comprises electronegative atoms which are able to reduce the charge at the oxygen atoms by their inductive effect. In particular, this is achieved by using aromatic compounds with fluorine substituents or heterocyclic aromatic compounds containing nitrogen atoms, for example. The right column of table 1 shows the partial charge Q at the oxygen atoms of several said anions in units of the elementary charge e. Data were calculated by a semiempirical quantum-mechanical computation. Obviously, the partial charge at the oxygen atoms is significantly reduced by the electronegative atoms fluorine and nitrogen.

The applicability of said electrolytes depends on conductivity, cycling behaviour stability against lithium, but also on compatibility with the cathode material. If highly oxidizing materials are used, it may be useful to apply electrolytes containing aromatic anions with fluorine substituents or heterocyclic aromatic anions, because use of chelate complexes with electronegative atoms results in a decrease of the energy of the highest occupied molecular orbital (HOMO) and consequently in an increased stability versus oxidation. Knowing the anodic potential limit of one electrolyte in accordance with the invention (cf. example 8), it is possible to estimate the anodic potential limit of similar structured compounds using a method of Yilmaz and Yurtsever (J. Electroanal. Chem., Vol. 261, 105–112, (1989)). The HOMO energies of several said anions are given in Table 1.

Several salts in accordance with the invention are produced by simple and inexpensive procedures, for example by crystallization from aqueous solution (cf. examples 1 and 2) or by a precipitation reaction (cf. example 3). Furthermore, the chemicals used for the production of lithium bis[1,2-benzenediolato(2-)-O,O']-borate(1-), lithium bis[salicylato(2-)]borate(1-), and tetraalkylammonium bis [1,2-benzenediolato(2-)-O,O']borate(1-) are inexpensive, so that production costs are low.

Formulas 1 to 7 show some structural formulas of compounds of the type according to the invention.

Structural formula 1:

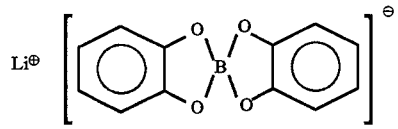

Empirical formula: LiB(C$_6$H$_4$O$_2$)$_2$

Systematic name: Lithium bis[1,2-benzenediolato(2-)-O, O']borate(1-)

Other names: Lithium bispyrocatecholatoborate, lithium biscatecholborate

Structural formula 2:

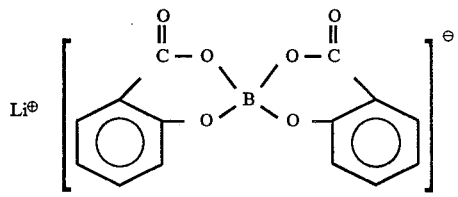

Empirical formula: LiB(C$_7$H$_4$O$_3$)$_2$

Systematic name: Lithium bis[salicylato(2-)]borate(1-)

Other name: Lithium bissalicylatoborate

Structural formula 3:

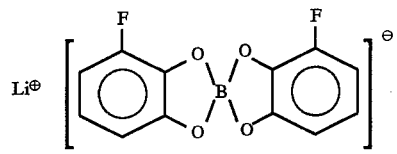

Empirical formula: LiB(C$_6$H$_3$FO$_2$)$_2$

Systematic name: Lithium bis[3-fluoro-1,2-benzenediolato(2-)-O,O']borate(1-)

Structural formula 4:

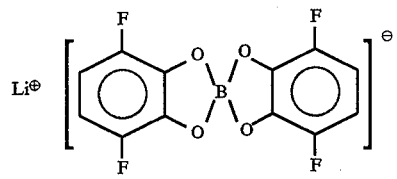

Empirical formula: Li[C$_6$H$_2$F$_2$O$_2$]

Systematic name: Lithium bis[3,6-difluoro-1,2-benzenediolato(2-)-O,O']borate(1-)

Structural formula 5:

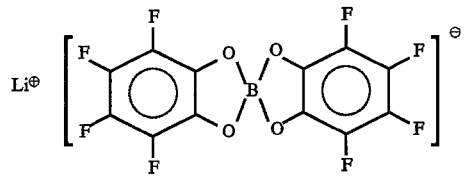

Empirical formula: LiB(C$_6$O$_2$F$_4$)$_2$

Systematic name: Lithium bis[3,4,5,6-tetrafluoro-1,2-benzenediolato(2-)-O,O']borate(1-)

Structural formula 6:

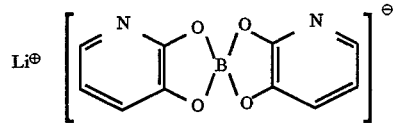

Empirical formula: LiB(C$_5$H$_3$NO$_2$)$_2$

Systematic name: Lithium bis[2,3-pyridinediolato(2-)-O, O']borate(1-)

Structural formula 7:

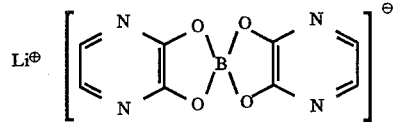

Empirical formula: LiB(C$_4$H$_2$N$_2$O$_2$)$_2$

Systematic name: Lithium bis[2,3-pyrazinediolato(2-)-O, O']borate(1-)

Another object of the invention is a galvanic cell comprising an anode, a cathode, and said electrolyte in accordance with the invention. Lithium, a lithium alloy or a Li$^+$ intercalating carbon electrode can be used as anode (cf. examples 10 and 11). A Li$^+$ intercalating electrode such as TiS$_2$, MoS$_2$ or vanadiumoxide can be used as cathode, where the equilibrium potential of the cathode should be lower than the anodic potential limit of the electrolyte. Salts comprising aromatic anions with fluorine substituents or heterocyclic aromatic anions should be preferred to avoid anodic oxidation of the electrolyte, if highly oxidizing cathode materials such as $MnO_2$, $NiO_2$ or $CoO_2$ are used. The electrolytes in accordance with the invention can be used both in primary and secondary lithium cells.

TABLE 1

| Ligand | Anion | $E_{HOMO} \cdot eV^{-1}$ | $Q \cdot e^{-1}$ |
| --- | --- | --- | --- |
| Catechol | $B(C_6H_4O_2)_2^-$ | −4,84 | −0,244 |
| 3-Fluorocatechol | $B(C_6H_3O_2F)_2^-$ | −5,16 | −0,234 |
| 3,6-Difluorocatechol | $B(C_6H_2O_2F_2)_2^-$ | −5,50 | −0,224 |
| Tetrafluorocatechol | $B(C_6O_2F_4)_2^-$ | −6,03 | −0,214 |
| 2,3-Dihydroxypyridine | $B(C_5H_3NO_2)_2^-$ | −5,20 | −0,227 |
| 2,3-Dihydroxypyrazine | $B(C_4H_2N_2O_2)_2^-$ | −5,65 | −0,209 |

EXAMPLE 1

Synthesis of Lithium Bis[1,2-benzenediolato(2-)-O,O'] borate(1-)

The salt is obtained by crystallization from concentrated aqueous solution.

Equation of the Reaction:

$$LiOH + B(OH)_3 + 2\ C_6H_4(OH)_2 \rightarrow LiB(C_6H_4O_2)_2 + 4H_2O$$

Procedure:

249.80 g (2.268 mole) catechol, 47.60 g (1.134 mole) $LiOH.H_2O$, 70.13 g (1.1344 mole) boric acid, and 130 ml $H_2O$ are heated to 90°–95° Cels. under inert gas, where a homogeneous brown solution forms. The flask is allowed to cool down to room temperature in the course of about 5 hours, where the substance crystallizes in the shape of colourless square plates. The flask is placed in a refrigerator for a night at +3° Cels. to increase the yield and then the mother lye is filtered off under inert gas applying the vacuum of a water jet pump. After drying for 39 hours at room temperature in the vacuum of an oil pump colourless crystals polluted by some brown substance (from the mother lye) are obtained. The mass is 169.78 g. It is a hydrate of the composition $LiB(C_6H_4O_2)_2 \cdot 2H_2O$ (cf. analysis). The substance is dried at 100°–110° Cels., in the vacuum of an oil pump until weight constancy (39 h). The crystals decompose yielding a colourless powder.

Raw yield: 144,84 g, 0.6191 mole, 54.6%

Purification:

300 ml acetonitrile are added to 143.66 g of the crude product. The mixture is heated to mild boiling under inert gas, and acetonitrile is added until a homogeneous solution forms. Colourless rectangular plates are obtained on cooling down overnight. The flask is placed in an ice bath for 1 hour, and in an ice sodium chloride bath for 1 hour. The mother lye is removed by decanting under an inert gas flow. Recrystallization is performed three times. The mother lye is yellowish green on first recrystallization and colourless on third recrystallization. Colourless needles of the composition $LiB(C_6H_4O_2)_2 \cdot 2AN$ (cf. analysis) are obtained after drying at room temperature for 4 hours in the vacuum of an off pump. Subsequently, the substance is decanted into a Sclenk flask, and dried in the vacuum of an oil pump inside a glove box, where the temperature is raised to 150° Cels. by small steps. Drying is continued until no further loss in weight is found, and no AN peak is detected by NMR spectroscopy at high transmitter and receiver power. A colourless powder is obtained.

Yield: 65.46 g, 0.2798 mole, 76.9% per recrystallization

Analysis:

Gravimetry:

After decomposition of the hydrate there is a loss of mass of 24.80 g (1.3766 mole $H_2O$), corresponding to 2.22 mole $H_2O$ per mole of the salt. On final drying the weight of the AN solvate decreases from 88.58 g to 65.46 g, corresponding to 23.12 g (0.5632 mole) AN, respectively 2.01 mole AN per mole of the salt.

pH titration:

Formally, the bis[1,2-benzenediolato(2-)-O,O']borate(1-) anion is composed of two catechol units, and one $B(OH)_4^-$ unit. The equivalence point was evaluated by titration with 0.5 n HCl at 50° Cels., and the boron content was calculated from it. Titration was carried out once for the crude product and three times for the purified product. The theoretical boron content is 4.621%. A boron content was found of 4.611% (relative error 0.22%) for the crude product, and of 4.622% (relative error 0.02%) for the purified product.

NMR:

The NMR-spectrum of the purified product in $DMSO-D_6$ shows a singlet at 6.5 ppm (TMS). This is a spectrum of the AA'BB' type, accidentally with equal chemical shifts of the protons as shown by comparative measurements using catechol dimethylether. In addition to the aromatic peak the spectrum of pure catechol shows a peak at 8.7 ppm (TMS) which is assigned to the OH groups. Neither the crude product nor the purified product shows this peak. In addition to the aromatic peak the crude product dried at room temperature shows another peak at 3.7 ppm (TMS) which is assigned to the crystal water. A water content of 2.13 mole $H_2O$ per mole of the salt is calculated for the hydrate from the integral curve. Additional to the aromatic peak the AN solvate dried at room temperature shows a signal at 2.0 ppm (TMS) which is assigned to the $CH_3$ group of acetonitrile. An AN content of 1.78 mole AN per mole of the salt results from the integral curve.

Water analysis:

A sample of the purified product was dissolved in THF and a water content of 56 ppm in accordance with K. F. was determined by calculating weight differences.

Thermal properties:

A sample of the substance is heated directly by the Bunsen time on a steel sheet. A greenish red coloured time as well as carbonization appears. Catechol is easy to inflame by the Bunsen flame on a steel sheet, where it melts and burns up completely colouring the flame yellow.

Solubility experiments in test glasses:

The substance is soluble in THF, 2-Me-THF, DME, PC, and of low solubility in dioxolane, diethylether, and toluene.

EXAMPLE 2

Synthesis of Tetramethylammonium Bis[1,2-benzenediolato (2-)-O,O']borate(1-)

The salt is obtained by crystallization from aqueous solution.

Equation of the Reaction:

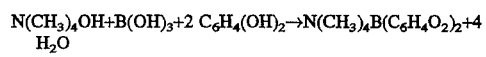

$$N(CH_3)_4OH + B(OH)_3 + 2\ C_6H_4(OH)_2 \rightarrow N(CH_3)_4B(C_6H_4O_2)_2 + 4 H_2O$$

Procedure:

86.98 g (0.7899 mole) catechol, 24.43 (0.39497 mole) boric acid, 360 ml 10% aqueous solution of tetramethylammonium hydroxide, and 300 ml water were heated up to 80°–85° Cels. under inert gas, where a slightly clouded yellowish brown solution forms. The hot solution is inoculated and allowed to cool down to room temperature overnight, where colourless quadrangular plates are obtained. Inoculation is necessary, because the product forms an oil otherwise. Inoculation crystals are obtained by taking a sample of the solution, heating in a test glass with the help of a heating fan, and cooling the solution to 0° Cels. in an ice bath while scratching with a glass rod.

The mother lye is decanted under an inert gas flow at room temperature and the crude product is dried for 16 hours in the vacuum of an oil pump. Subsequently, drying is continued for 6.5 hours at 60°–70° Cels. in the vacuum of an oil pump. No change of the crystals is visible; the loss of weight is only 0.3%. The salt crystallizes free of crystal water.

Raw yield: 67.39 g, 0.2238 mole, 56,6%
Purification:
64.94 g of the raw product and 100–150 ml acetone are heated to 50°–55° Cels. under inert gas resulting in a homogeneous brown solution which is allowed to cool down to room temperature, and inoculated. Colourless rectangular flat needles are obtained. After standing overnight the flask is placed in an ice bath for 2 hours and in an ice sodium chloride bath for 45 minutes. The mother lye is decanted under an inert gas flow. Altogether, recrystallization is performed 5 times. After the fifth recrystallization the mother lye is clear and colourless. The colourless crystals are dried in the vacuum of an off pump for four hours at room temperature, where they decompose yielding a colourless powder. Subsequently, the substance is dried for 3 hours at 50°–70° Cels. in the vacuum of an oil pump. No loss of weight is detected at this. Obviously, the crystals are an acetone solvate which already decomposes at room temperature in the vacuum of an oil pump.

Yield: 33.57 g, 0.1147 mole, 87.6% per recrystallization
Analysis:
NMR:
The NMR spectrum of the crude product in DMSO shows a peak at 3.0 ppm (TMS) which is assigned to the methyl groups, as well as a peak at 6.5 ppm (TMS) which is assigned to the protons of the bis[1,2-benzenediolato(2-)-O,O']borate(1-) anion. Furthermore, some small peaks are found in the range of 6.5–6.9 ppm (TMS) which can be obviously attributed to impurities. $H_2O$ is not detected. The purified product shows only the two peaks at 3.0 and 6.5 ppm (TMS). The ratio of integrals agrees with the theoretical value within the accuracy in measurement Solubility experiments in test glasses:
The substance is soluble in PC, dioxolane, and AN, scarcely soluble in DME, and THF, and of low solubility in toluene.

EXAMPLE 3

Synthesis of Butyltriethylammonium Bis[1,2-benzenediolato(2-)-O,O']borate(1-)

The salt is synthesized by precipitation of lithium chloride in acetonitrile.

Equation of the Reaction:

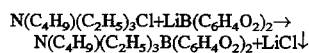

Procedure:
5.49 g (23.47 mmole) lithium bis[1,2-benzenediolato(2-)-O,O']borate(1-), 4.53 g (23.38 mmole) butyltriethylammonium chloride and 30 ml acetonitrile are stirred in an Erlenmeyer flask at room temperature inside a glove box. A colourless suspension of lithium chloride forms. Filtration yields a colourless precipitate of small crystals of lithium chloride as well as a clear colourless filtrate. The flitrate is evaporated to dryness at room temperature in the vacuum of an oil pump, and the colourless solid substance is dried for 17 hours at room temperature.

Raw yield: 8.59 g, 22.29 mmole, 95.4%
Purification:
19 ml acetonitrile are added to 8.18 g of the substance under inert gas at room temperature. A clear colourless solution is obtained. Then 50 ml diethylether are added resulting in a slightly clouded solution. Filtration under inert gas results in a clear colourless solution as well as in a small fraction of a colourless solid (probably LiCl). Storing for one night in a cold save (–25° Cels.) yields colourless plates. The mother lye is decanted under an inert gas flow. Recrystallization is carried out twice. Then the substance is dried in the vacuum of an oil pump at room temperature for two hours, and at 50°–65° Cels. for 19 hours. The loss of mass is only 0.6%; no solvate is formed.

Yield: 6.92 g, 17.96 mmol, 92.0% per recrystallization
Analysis:
NMR:
As expected the NMR spectrum is a superposition of the spectra of pure butyltriethylammonium chloride, and of lithium bis[1,2-benzenediolato(2-)-O,O']-borate(1-).

Melting point: 86°–87° Cels.

EXAMPLE 4

Synthesis of Lithium Bis[salicylato(2-)]borate(1-)
Equation of the Reaction:

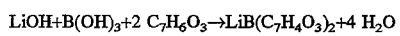

Procedure:
244.90 g (1.7731 mole) salicylic acid, 37.20 g (0.8860 mole) $LiOH.H_2O$, 54.82 g (0.8866 mole) boric acid, and 100 ml $H_2O$ are heated to mild boiling. A homogenous colourless solution forms. On cooling down to room temperature a voluminous colourless precipitate of small crystals is obtained which cannot be filtered. Crystals for inoculation are taken; heating to the boiling point is repeated; the flask is placed in a Dewar containing hot water, and inoculated. On cooling down a precipitate of small crystals is obtained. After 2 days the flask is placed in a refrigerator for 7 hours at +10° Cels., and for 2 days at 0° Celsius. The flask is supplied with a connecting tube containing a glass filter as well as with a second flask, and the mother lye is filtered off at 0° Cels. applying the vacuum of a water jet pump. The substance is dried in the vacuum of an oil pump for 7 hours at 0° Cels., end for approximately 50 hours at room temperature. 197.76 g of product are obtained. Drying for 280 hours at 80°–180° Cels. reduces the weight to 184.76 g. After taking a sample drying is continued for 93 hours at 170°–180° Cels. reducing the weight from 184.59 g to 183.15 g.

Raw yield: 183.15 g, 0.63194 mole, 71.2%
Purification:
179.58 g of the crude product and 850 ml acetonitrile are heated to mild boiling under inert gas. A slight cloudiness is obtained which does not vanish on raising the volume of the solution to 960 ml. The solution is filtered under inert gas and cooled down to room temperature. A layer of colourless crystals forms at the wall of the flask. The flask is stored in a refrigerator for 3 hours at 0° Cels., and in a cold save for one night at –25° Celsius. Then the mother lye is decanted under an inert gas flow. Altogether, recrystallization is performed three times. On second recrystallization a cloudiness is visible again (filtration); on third recrystallization the solution remains clear. Drying for 1.5 hours at room temperature in the vacuum of an oil pump yields 151.84 g. Then drying is continued for 171 hours until weight constancy in the vacuum of an oil pump, where the temperature is raised slowly from 80°–90° Cels. to 150°–155° Celsius. A colourless powder is obtained.

Yield: 118.11 g, 0.4073 mole, 86.4% per recrystallization

Analysis:

Gravimetry:

The mass decreases by 11.4 g (0.6350 mole $H_2O$) on drying the crude product at elevated temperature, corresponding to 1.00 mole $H_2O$ per mole of the salt. The mass of the final product decreases by 33.73 g (0.8216 mole AN) on drying, corresponding to 2.02 mole AN per mole of the salt. The solvates are of the composition $LiB(C_7H_4O_3)_2 \cdot H_2O$, and $LiB(C_7H_4O_3) \cdot 2AN$.

pH-titration:

Formally the bis[salicylato(2-)]borate(1-) anion is composed of two salicylic acid units and one $B(OH)_4^-$ unit. Therefore, lithium bis[salicylato(2-)]borate(1-) reacts acidic on hydrolysis in aqueous solution The equivalence point was evaluated by titration at 70° Cels. using 0.1 n NaOH. Theoretically, the expected quantity of lye is 1 mole NaOH per mole of the salt. Titration was carried out once for the crude product and three times for the purified product. A consumption of lye was found of 0.996 mole NaOH per mole of the salt for the crude product, and of 0.9992 mole NaOH per mole of the salt for the purified product.

NMR:

In DMSO-D6 the crude product dried at room temperature shows a multiplet with its centre at 7.3 ppm (TMS) which is assigned to the aromatic residue, as well as a singlet at 3.5 ppm which is referred to water. A water content of 1.01 mole $H_2O$ per mole of the salt results from the integral curve. The crude product dried at elevated temperature still shows a small water peak which is not to evaluate quantitatively, because commercially available DMSO as well as TMS always show a small content of residual water as proved by comparative measurements using the pure solvent. The product recrystallized from AN and dried at room temperature shows a singlet at 2.0 ppm (TMS) in addition to the aromatic multiplet which is assigned to AN bonded in the solvate. An AN content of 1.70 mole per mole of the salt results from the integral curve. The value which is somewhat to low probably refers to loss by evaporation on filling the tube inside a glove box. The purified product dried at elevated temperature only shows a multiplet at 7.3 ppm (TMS). At a high transmitter and receiver power a small peak is perceptible at 2.0 ppm which is close to the detection limit of the method and cannot be evaluated quantitatively. A comparative spectrum of salicylic acid was recorded showing a broad peak at 12.4 ppm (TMS) which is assigned to the protons of the COOH and OH groups. This peak is not detectable in the NMR spectrum of lithium bis[salicylato (2-)]borate(1-).

Water Analysis:

A sample of the substance was dissolved in PC and the water content in accordance with K. F. was determined by calculating weight differences. A $H_2O$ content was found of 2200 ppm for the crude product, and of 64 ppm for the purified product.

Thermal properties:

A sample of the dried product is heated directly by the Bunsen flame on a stainless steel sheet. The substance burns colouring the flame green and red; carbonization occurs.

Solubility experiments in test glasses:

The substance is soluble in THF, 2-Me-THF, DME, PC, dioxolane, and acetone, and of low solubility in diethylether. However, colourless crystals (solvate) form in THF and 2-Me-THF on standing for a long time (some hours up to some days). The substance tends to form supersaturated solutions.

EXAMPLE 5

Conductivity

The conductivity of some electrolytes was measured using a small measuring cell and a commercially available bridge. The temperature was measured with a mercury thermometer. The specific conductivities, as shown in table 2, are measured at arbitrary concentrations. This are not $\chi_{max}$-values. The values are not very precise; they are meant to serve for a rough estimation of attainable conductivity.

TABLE 2

| System | $\upsilon$ °C.$^{-1}$ | $\kappa$ mS$^{-1}$ cm |
|---|---|---|
| 1.231 molal $LiB(C_6H_4O_2)_2$ in PC | 27 | 0,6 |
| 1.184 molal $LiB(C_6H_4O_2)_2$ in THF | 29 | 1,4 |
| 0.899 molal $LiB(C_6H_4O_2)_2$ in DME | 26 | 1,7 |
| 0.595 molal $LiB(C_6H_4O_2)_2$ in 2-Methyl-THF | 29 | 0,4 |
| 1.11 molal $LiB(C_6H_4O_2)_2$ in a mixture of 45.7 weight % PC und 54.3 weight % DME | 25 | 3,0 |
| 0.519 molal $N(CH_3)_4B(C_6H_4O_2)_2$ and 0.293 molal $LiB(C_6H_4O_2)_2$ in PC | 17 | 2,8 |
| 0.561 molal $N(CH_3)_4B(C_6H_4O_2)_2$ and 0.271 molal $LiB(C_6H_4O_2)_2$ in a mixture of 60.4 weight % THF and 39.6 weight % PC | 18.5 | 5,1 |
| 0.400 molal $N(CH_3)_4B(C_6H_4O_2)_2$ and 0.555 molal $LiB(C_6H_4O_2)_2$ in a mixture of 52.8 weight % PC and 47.2 weight % DME | 23 | 5,5 |
| 0.713 molal $LiB(C_7H_4O_3)_2$ in DME | 27 | 0,8 |
| 0.775 molal $LiB(C_7H_4O_2)_2$ in PC | 29 | 0,4 |
| 0.840 molal $LiB(C_7H_4O_2)_2$ in a mixture of 59.8 weight % PC and 40.2 weight % DME | 26 | 1,7 |

EXAMPLE 6

CV of the Residual Current

In each case 5 cyclic voltammograms were recorded in series using a stainless steel electrode with an area of 0.503 cm$^2$. The potential was swept from the open-circuit potential to 0 mV vs. Li/Li$^+$, and back to the open-circuit potential again at a potential sweep rate of 20 mV/s. Lithium bis[1, 2-benzenediolato(2-)-O,O']borate(1-) was investigated in organic solvents, and in mixtures of organic solvents as well as with tetraalkylammonium bis[1,2-benzenediolato(2-)-O, O']borates(1-) as an additive. The cyclic voltammograms of the residual current of some systems are shown in FIG. 1 to FIG. 4. The curves are scarcely structured, and don't show any reduction peak which contrasts markedly with the residual current. No reduction of the tetramethylammonium ions is visible (cf. FIG. 1, and 2).

EXAMPLE 7

CV for Lithium Deposition

In each case 5 cyclic voltammograms were recorded in series using a stainless steel electrode with an area of 0.503 cm$^2$. The experiments were carried out without exchanging the working electrode immediately after having finished the cyclic voltammograms of residual current. The potential was swept from the open-circuit potential to −500 mV vs. Li/Li$^+$, then to +3000 mV vs. Li/Li$^+$, and finally back to the open-circuit potential at a potential sweep rate of 20 mV/s.

The efficiency was evaluated by numerical integration in the I-t graph. FIG. 5 to 9 show the cyclic voltammograms of some systems. The mean efficiency of 5 cycles is shown on the right side of the CVs.

Systems containing PC as a solvent or mixtures of PC and ethers show relatively high efficiencies, as can be seen in the shown cyclic voltammograms, whereas systems containing pure DME, 2-Me-THF, and THF (not shown here) as a solvent yield only low efficiencies. Tetramethylammonium ions scarcely influence the cycling behaviour.

EXAMPLE 8

Anodic Potential Limit

Figure 10:
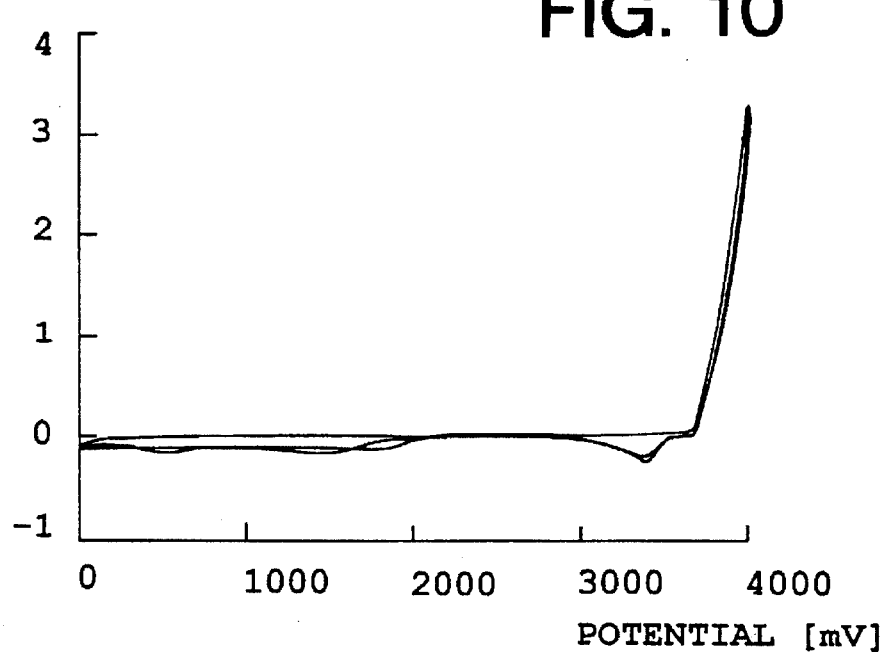
FIGS. 10 to 12 show magnification of the anodic region for two systems of the electrolyte of the disclosed invention.
Figure 11:
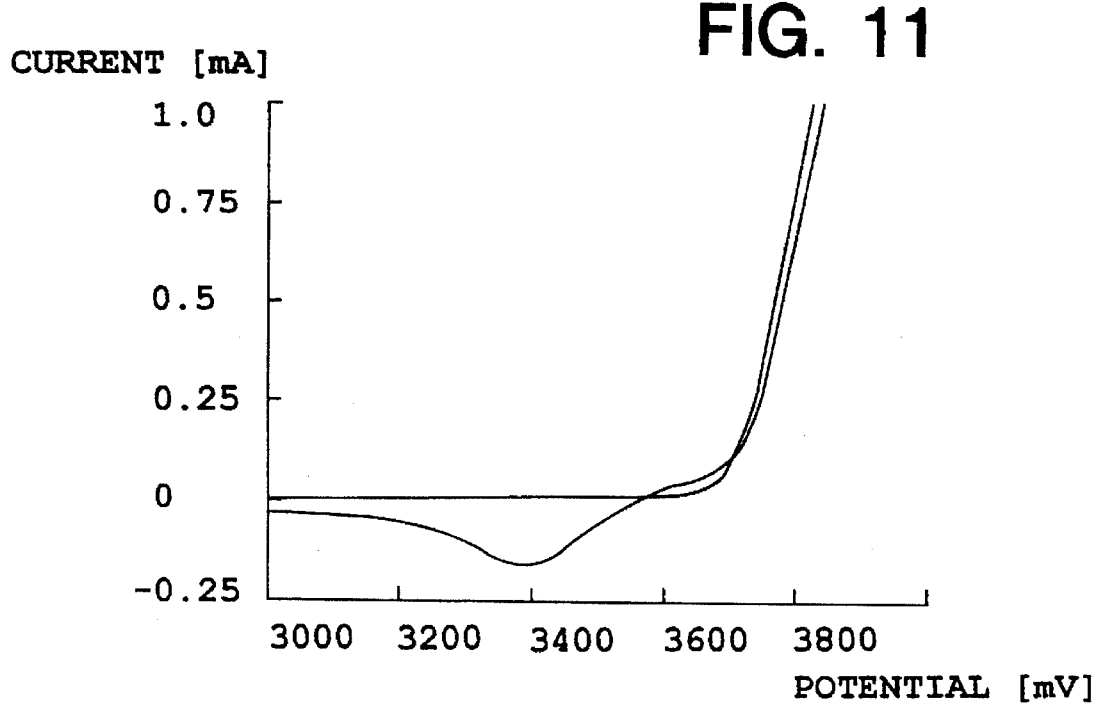
Figure 12:
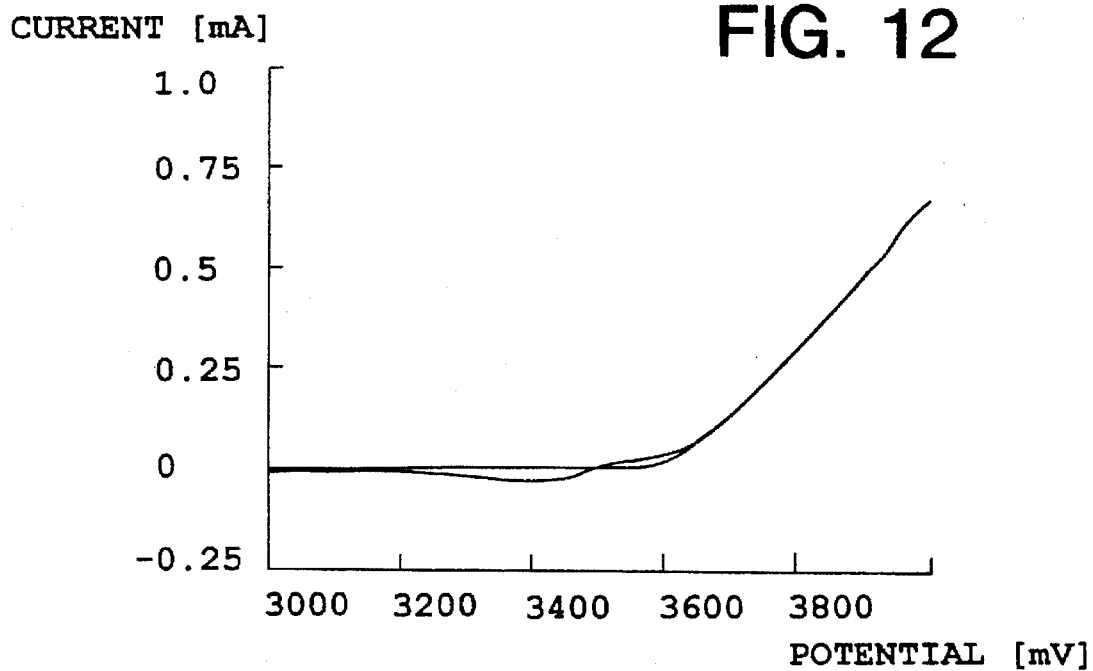

In each case 5 cyclic voltammograms were recorded in series to evaluate the anodic potential limit using a stainless steel electrode with an area of 0.503 cm$^2$. The potential was swept at a sweep rate of 20 mV/s from the open circuit potential to 4000 mV vs. Li/Li$^+$, then to 0 mV vs. Li/Li$^+$, and finally back to the open circuit potential. A typical CV is shown in FIG. 10. FIGS. 11, and 12 show a magnification of the anodic region for two systems. The anodic potential limit of about 3.6 V vs. Li/Li$^+$ depends scarcely on the composition of the solution.

EXAMPLE 9

Cycling on Stainless Steel

Figure 13:
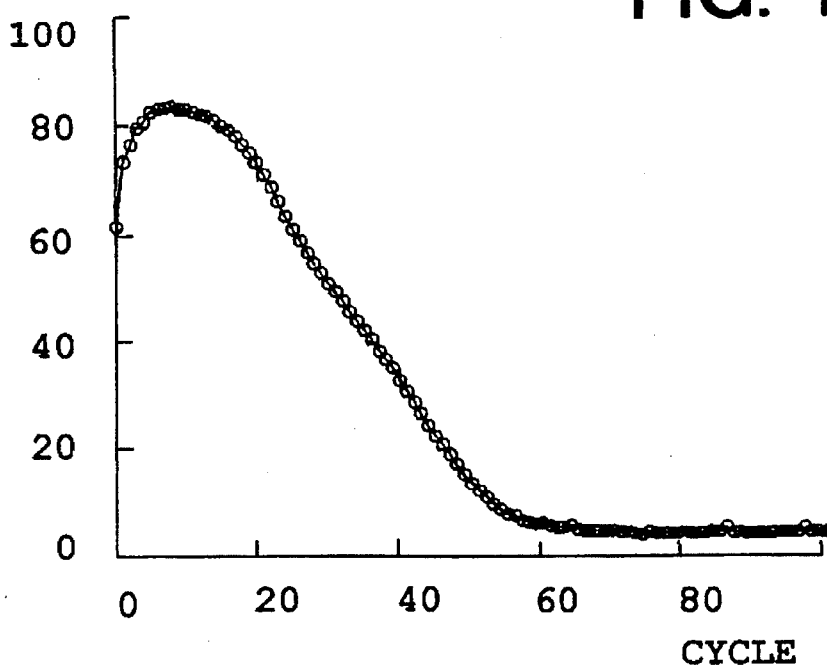
FIGS. 13 to 16 show galvanostatic cycling experiments of the electrolyte of the disclosed invention.
Figure 14:
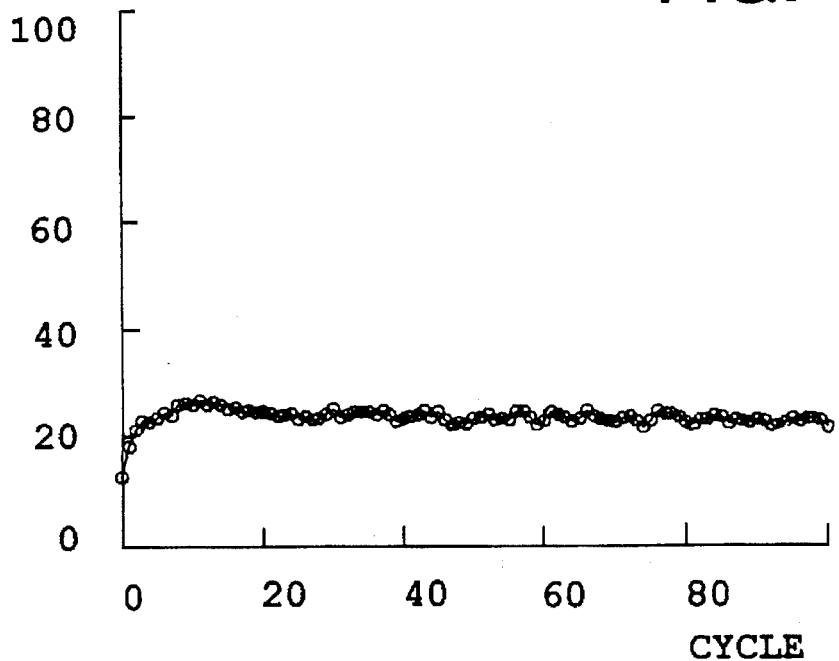
Figure 15:
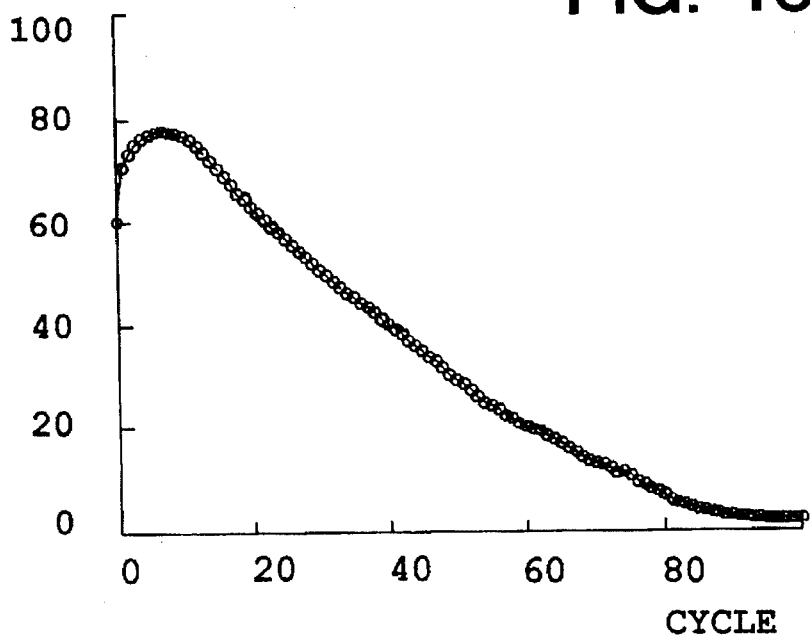

Galvanostatic cycling experiments were carried out at a charge density of 100 mC/cm$^2$, and at a current density of 1 mA/cm$^2$ to evaluate cycling efficiency using a stainless steel electrode with an area of 0.503 cm$^2$. Some examples are shown in FIGS. 13–15. In solutions containing PC the efficiency is relatively high at the former cycles, comes up to a maximum, and decreases finally to small values. Lithium deposits in the shape of grey needles which do not dissolve on exposure to the electrolyte for some days. Hence the loss of efficiency is referred to a loss of contact of lithium. Cycling efficiency is low in solutions containing solely DME, THF, or 2-Methyl-THF as a solvent. No significant influence of tetraalkylammonium salts on cycling efficiency is observed. No visible change of the investigated solutions (formation of gas bubbles or colouration) was observed.

EXAMPLE 10

Cycling on Carbon

Figure 16:
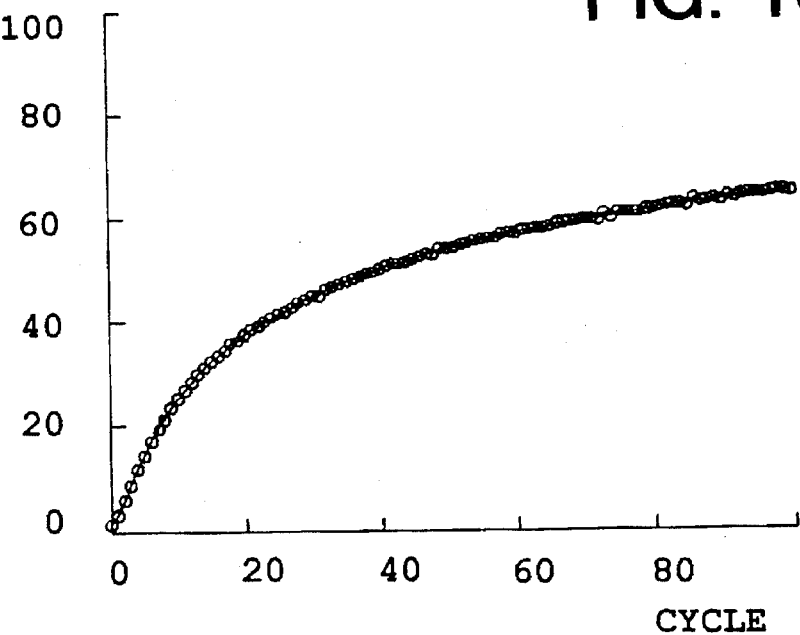
Figure 17:
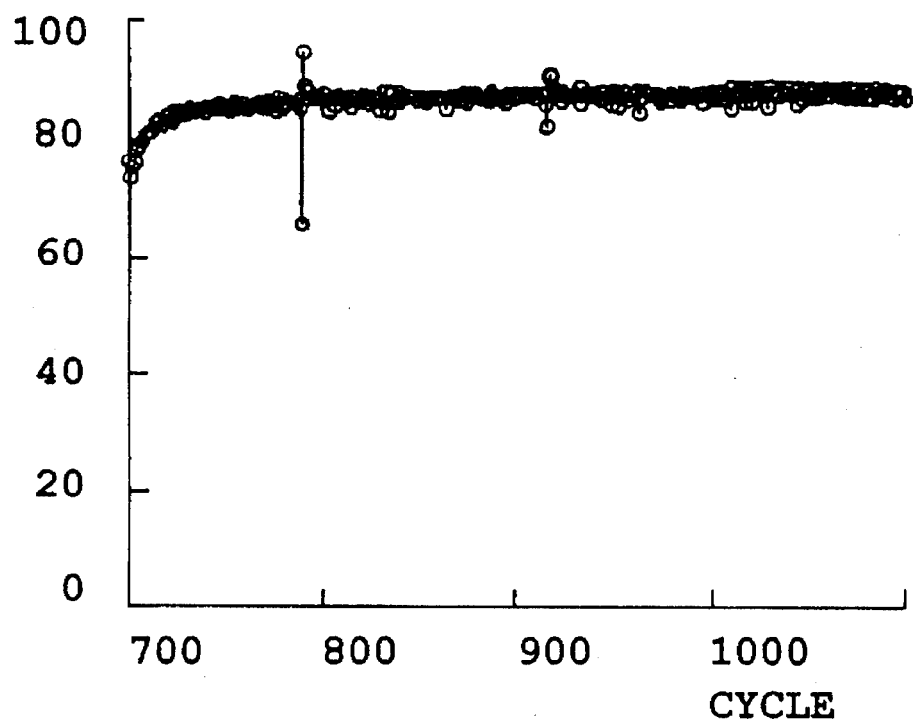

A cycling experiment was carried out at a charge density of 100 mC/cm$^2$, and at a current density of 1 mA/cm$^2$ using a glassy carbon electrode with an area of 0.0707 cm$^2$ (3 mm diameter). The potential limit was fixed to 1500 mV vs. Li/Li$^+$. A solution was arbitrarily chosen as an electrolyte which contained 0.561 mol/kg tetrmethylammonium bis[1,2-benzenediolato(2-)-O,O']borate(1-), and 0.271 mol/kg lithium bis[1,2-benzenediolato(2-)-O,O']borate(1-) in a mixture containing 39.6 weight % PC, and 60.4 weight % THF. Altogether, 1100 cycles were run with stops of 5 minutes after cycle 100, 145 minutes after cycle 300, 3 minutes after cycle 400, and 94 minutes after cycle 700. The cycling efficiency increases continually at this. FIG. 16 shows the former 100 cycles, and FIG. 17 the final 400 cycles. The curves show the expected appearance. The efficiency is low in the former cycles, because the mean part of charge is consumed by irreversible processes (e.g. formation of a covering layer). The efficiency increases to high values at increasing number of cycles. No change of the electrolyte (formation of gas bubbles or coloration) was observed.

EXAMPLE 11

Cycling on Lithium

A half cell was used to evaluate cycling efficiency. It consists of a stainless steel working electrode covered with a 0.1 mm thick layer of lithium which was pressed onto the surface, a lithium foil as a counter electrode, a separator and a cell-container made of glass. The distance between the electrodes was about 3 mm, the area of the electrode 1 cm$^2$, and the volume of the electrolyte 3 or 4 cm$^3$. The separator (Celgard 2400) was made of polypropylene. The solution contained 0.400 mol/kg tetramethylammonium bis[1,2-benzenediolato(2-)-O,O']borate(1-) and 0.555 mol/kg lithium bis[1,2-benzenediolato(2-)-O,O']borate(1-) in a mixture of 52.8 weight % PC and 47.2 weight % DME. Cycling was carried out at a current density of 0.5 mA/cm$^2$ on charging, and at a current density of 1.0 mA/cm$^2$ on discharging, as well as at a DOD of 22.6%. The pressed-on charge was 101.62 C. Grey dendrites formed on the counter electrode during first cycle. No formation of gas bubbles, and no colouration of the electrolyte was observed. At the end of cycling the space between the electrodes was filled with a flurry of lithium. 4.90 cycles were achieved. Various modifications in the structure, function, steps and features of the disclosed invention may be made by one skilled in the art without departing from the scope and extent of the claims.

I claim:

1. An electrolyte for use in a galvanic cell comprising at least one compound represented by the formula ABL$_2$, wherein A is lithium or a quarternary ammonium ion, B is boron, and L is a bidentate ligand, which is linked to the central boron atom by two oxygen atoms, with the proviso that the electrolyte comprises at least one lithium salt.

2. The electrolyte in accordance with claim 1 comprising at least one compound represented by the formula ABL$_2$, which is dissolved in an organic solvent, a mixture of organic solvents, one or more polymers, or a mixture of one or more polymers and at least one organic solvent.

3. The electrolyte in accordance with claim 1, wherein the quarternary ammonium ion is represented by the formula NR$_4$, NR$_3^A$ R$^B$, NR$_2^C$ or NR$^C$R$^D$, where R, R$^A$, R$^B$, R$^C$ and R$^D$ represent organic residues.

4. The electrolyte in accordance with claim 1, comprising at least one compound represented by the formula ABL$_2$, which is dissolved in propylene carbonate or butylene carbonate, or in a mixture of solvents comprising at least propylene carbonate, butylene carbonate or ethylene carbonate.

5. The electrolyte in accordance with claim 1, wherein the ligand L comprises at least one aromatic group.

6. The electrolyte in accordance with claim 5, wherein the ligand L comprises at least one aromatic six-membered ring.

7. The electrolyte in accordance with claim 6, wherein the aromatic six-membered ring comprises at least one fluorine atom linked to the ring, and at least one nitrogen atom within the ring.

8. The electrolyte in accordance with claim 7, wherein the ligand L is represented by the formula C$_6$H$_3$FO$_2$, C$_6$H$_2$F$_2$O$_2$, C$_6$HF$_3$O$_2$ or C$_6$F$_4$O$_2$.

9. The electrolyte in accordance with claim 7, wherein the ligand L is represented by the formula C$_5$H$_3$NO$_2$ or C$_4$H$_2$N$_2$O$_2$.

10. The electrolyte in accordance with claim 6, wherein the ligand L is represented by the formula C$_6$H$_{(4-x)}$R$_x$O$_2$, where x is an integer from 0 up to 4, and R is an alkyl residue.

11. The electrolyte in accordance with claim 1, wherein the compound ABL$_2$ is lithium bis[1,2-benzenediolato(2-)-

O,O']borate(1-) represented by the formula $LiB(C_6H_4O_2)_2$ or a tetraalkylammonium bis[1,2-benzenediolato(2-)-O,O']borate(1-) represented by the formula $NR_4B(C_6H_4O_2)_2$ or $NR_3^A R^B B(C_6H_4O_2)_2$, where R, $R^A$, and $R^B$ are alkyl residues.

12. The electrolyte in accordance with claim 1, wherein the compound $ABL_2$ is lithium bis[1,2-benzenediolato(2-)]borate(1-) represented by the formula $LiB(C_6H_4O_2)_2$.

13. The electrolyte in accordance with claim 1, wherein the compound $ABL_2$ is lithium bis[salicylato(2-)]borate(1-) represented by the formula $LiB(C_7H_4O_3)_2$.

14. The electrolyte in accordance with claim 1 wherein the at least one compound represented by the formula $ABL_2$ is dissolved in an organic solvent, a mixture of organic solvents, one or more polymers, or a mixture of one or more polymers and at least on organic solvent, and wherein the ligand L comprises at least one aromatic group.

15. A galvanic cell comprising a cathode, an anode and an electrolyte which comprises at least one compound represented by the formula $ABL_2$, wherein A is lithium or a quaternary ammonium ion, B is boron, and L is a bidentate ligand, which is linked to the central boron atom by two oxygen atoms, with the proviso that the electrolyte comprises at least one lithium salt.

16. The galvanic cell according to claim 15 wherein the at least one compound represented by the formula $ABL_2$ is dissolved in propylene carbonate or butylene carbonate, or in a mixture of solvents comprising at least propylene carbonate, butylene carbonate, or ethylene carbonate.

17. The galvanic cell according to claim 15 wherein the ligand L comprises at least one aromatic group.

18. The galvanic cell according to claim 15 wherein the ligand L is represented by the formula $C_6H_3FO_2$, $C_6H_2F_2O_2$, $C_6HF_3O_2$, or $C_6F_4O_2$.

19. The galvanic cell according to claim 16 wherein the ligand L is represented by the formula $C_5H_3NO_2$ or $C_4H_2N_2O_2$.

20. The galvanic cell according to claim 15 wherein the compound $ABL_2$ is lithium bis[1,2-benzenediolato(2-)]borate (1-) represented by the formula $LiB(C_6H_4O_2)_2$.

* * * * *